United States Patent [19]

Oda et al.

[11] Patent Number: 4,877,582

[45] Date of Patent: Oct. 31, 1989

[54] CHEMICAL SENSOR DEVICE WITH FIELD EFFECT TRANSISTOR

[75] Inventors: Shohei Oda; Osamu Seshimoto; Tohru Sueyoshi; Hiroyuki Amano, all of Saitama, Japan

[73] Assignee: Fuji Photo Film Co., Ltd., Kanagawa, Japan

[21] Appl. No.: 87,508

[22] Filed: Aug. 20, 1987

[30] Foreign Application Priority Data

Aug. 20, 1986 [JP] Japan .................................. 61-194973

[51] Int. Cl.⁴ .............................................. G01N 27/00
[52] U.S. Cl. ..................................... 422/68; 435/291; 436/806
[58] Field of Search ................ 118/642; 354/307, 309, 354/316; 356/244, 246; 422/56–60, 68, 50, 104; 436/164, 165, 169–170, 806; 435/291

[56] References Cited

U.S. PATENT DOCUMENTS

| 1,806,232 | 5/1931 | Abe ........................................ 354/307 |
| 2,577,440 | 12/1951 | Wolff .................................... 354/307 |
| 3,595,158 | 7/1971 | Long ...................................... 354/307 |
| 3,831,432 | 8/1974 | Cox . | |
| 4,005,463 | 1/1977 | Kowalski ............................. 354/307 |
| 4,020,830 | 5/1977 | Johnson et al. . | |
| 4,062,750 | 12/1977 | Butler . | |
| 4,144,306 | 3/1979 | Figueras .......................... 436/170 X |
| 4,323,536 | 4/1982 | Columbus ............................. 422/58 |
| 4,390,343 | 6/1983 | Walter ............................. 436/170 X |
| 4,512,870 | 4/1985 | Kohara et al. . | |
| 4,582,684 | 4/1986 | Vogel et al. .......................... 422/57 |

FOREIGN PATENT DOCUMENTS

2101806 1/1983 United Kingdom .

*Primary Examiner*—Michael S. Marcus
*Attorney, Agent, or Firm*—Jules E. Goldberg

[57] ABSTRACT

A chemical sensor having a field-effect transistor as an electronic transducer and used for the analysis of specific constituents in a liquid, the chemical sensor comprising means which permits an externally supplied sample solution to reach a chemical receptor of said chemical sensor but substantially prevents external light from reaching said field effect transistor.

14 Claims, 6 Drawing Sheets

CHEMICAL SENSOR DEVICE WITH FIELD EFFECT TRANSISTOR

BACKGROUND OF THE INVENTION

1. Field of the Invention

The present invention relates to a chemical sensor device using a field effect transistor.

2. Prior Art

Recently, a biological detecting means, a so-called "biosensor", has been given attention in the field of medical and health care and the development thereof has been progressed. The biosensor is basically composed of two essential parts, that is, a biochemical receptor (BR) such as immobilized enzymes on membranes, antibodies or microorganisms, and an electronic transducer (ET). The BR reacts chemically with a substance to be detected, and the ET converts the chemical reaction into a measurable electrical signal. Classical half cells, that is, electrodes, have been used as the electronic tranSducer, but their performance is not enough for use as a biOsensor. Hence, semiconductor elements are expected to be developed.

Examples of semiconductor elements which have been developed include a field effect transistor (hereinafter abbreviated to "FET"), a metal insulator semiconductor (MIS), and the like. Because the FET is advantage in compositeness and miniaturization, an ion sensitive FET (abbreviated to "ISFET") formed by combining the FET as an electronic transducer with an ion sensitive membrane have been rapidly developed in the recent years. Further, a biosensor or biochemical FET having a membrane immobilizing a biological active substance has been investigated. The FET, however, has light-sensitivity caused by the light-conductivity of Si. Accordingly, a darkroom or a darkbox is necessary in the measurement using the ISFET or the like, so that the operation of measurement is troublesome.

SUMMARY OF THE INVENTION

An object of the present invention is to eliminate the necessity of the darkroom or darkbox in the measurement using an ion- or molecule-sensitive sensor in which the aforementioned FET is used as an electronic transducer, so as to thereby make the operation of measurement simple and efficient.

To attain the foregoing object of the invention, the inventors provide a chemical sensor using an FET including means which permits an externally supplied sample liquid from outside to reach a detecting part of the FET sensor but substantially prevents external light from reaching at least an FET portion of the FET sensor. The meaning of the words "substantially prevents light from reaching an FET portion" is that the intensity of light at the FET portion is reduced to be below 1/20, preferably below 1/100 compared to that at the surface of the housing.

The chemical sensor according to this invention comprises a chemical receptor for chemically reacting a specific substance in sample liquid, a field effect transistor connected to the chemical receptor for converting the chemical reaction into measureable electrical signal, a housing having light-shielding properties for installing the chemical receptor and the field effect transistor therein, the housing having an opening for receiving and leading the sample liquid externally supplied into the housing, and light shielding means for permitting the sample liquid to reach the chemical receptor and substantially preventing external light from reaching the field transistor.

DETAILED DESCRIPTION OF THE INVENTION

Specific examples of the means according to this invention which permits a sample liquid to reach the detection part of the FET sensor but prevents light from reaching the FET portion are as follows.

(1) The FET sensor is housed in a light-shielding package having an opening portion communicated with a chemical receptor, the opening portion being covered with a light-absorptive but liquid-permeable member.

The liquid-permeable member may be homogeneous or heterogeneous as to form a dispersion containing a discontinuous phase, or it may be porous.

For example, the homogeneous liquid-permeable member is formed of a hydrophilic polymer containing light-absorptive dye. A typical example of the homogeneous liquid-permeable member is a gelatin membrane containing water-soluble dye, such as oxonol dye.

It is preferable that the disperse phase contains light-absorptive particles. A typical example of the disperse-phase liquid-permeable member is a gelatin membrane containing carbon black. Further, dye and the like may be contained in the continuous phase.

The porous liquid-permeable member may be formed of light-absorptive material having pores or may be formed of light-non-absorptive material having pores and containing light-absorptive particles. For example, the liquid-permeable member may be formed by containing carbon black in the solid phase or pores of porous cellulose acetate prepared by a phase-separating method or the like.

All parts of the liquid-permeable member need not always be light-absorptive, but only a part near to the FET sensor or a part far from the FET sensor may be light-absorptive.

(2) The FET sensor is housed in a package which permits the externally supplied sample liquid to reach the chemical receptor of the FET sensor but substantially prevents light from reaching the FET portion of the FET sensor.

Embodiments of the present invention will be described in detail hereunder with reference to the drawings.

Figure 1A:
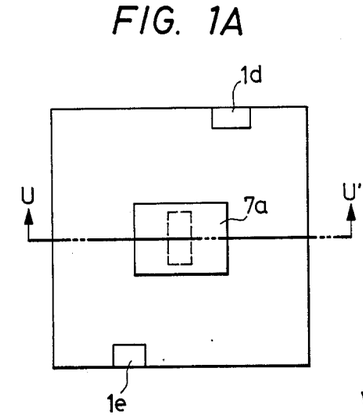
FIGS. 1A, 2A, 3B, 5A and 6A are plan views of a chemical sensor according to the present invention.
Figure 1B:
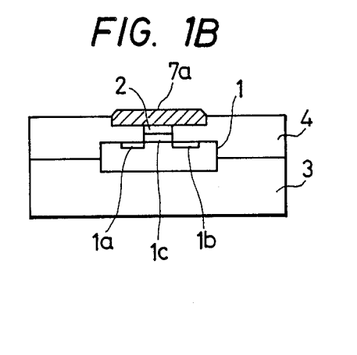
FIGS. 1B, 2B, 3C, 4A, 5B, 6B and 7B are sectional views of the chemical sensor according to the present invention.

FIG. 1A is a plan view showing a first embodiment of the FET sensor according to the present invention, and FIG. 1B is a sectional view taken along the line U—U' of FIG. 1A. In FIG. 1B, the FET 1 has a source region 1a, a drain region 1b and a gate 1c. A chemical receptor 2 is provided on the surface of the gate 1c. The chemical receptor 2 is, for example, an immobilized enzyme membrane. The FET 1 is supported between a lower frame 3 and an upper frame 4 each having light-shielding property. The light-shielding lower and upper frames 3 and 4 are, for example, made of polystyrene containing 4% by weight of carbon black in the form of dispersion, and are closely in contact with each other (the lower and upper frames may be united to one body). The upper frame 4 has an opening in its upper surface, the opening being communicated with the chemical receptor 2 of the sensor. The opening is covered with a liquid-permeable and light-absorptive porous member 7a, such as cotton cloth, cotton knitting, long-staple cellulose nonwoven fabric, or the like-soaked in or coated by opaque pigment solution. The sample liquid can permeate through the porous member 7a, but light can not permeate through the porous member 7a so that the light can not reach the FET portion of the sensor. The porous member 7a must be chemically inactive to the sample liquid. If the sample liquid has its origin in a living body, the porous member 7a must be biochemically inactive. If the sample liquid is blood, it is preferable that the porous member 7a is made of material free from hemolysis. The reference numerals 1d and 1e designate terminals for electrical connection to the source and drain regions of the FET 1.

Figure 2A:
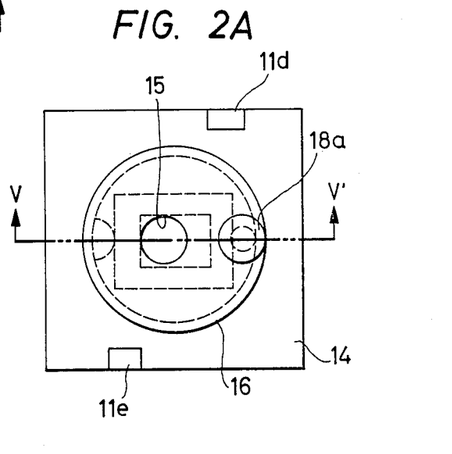
Figure 2B:
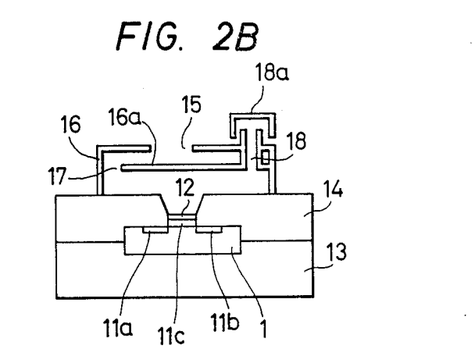

FIG. 2A is a plan view showing a second embodiment of the FET sensor package, and FIG. 2B is a sectional view taken along the line V—V' of FIG. 2A. In FIGS. 2A and 2B, the FET 11 has a source region 11a, a drain region 11b and a gate 11c. A chemical receptor 12 is provided on the surface of the gate 11c. The chemical receptor 12 is, for example, and immobilized enzyme membrane. The FET 11 is supported between a lower frame 13 and an upper frame 14 each having light-shielding property. The light-shielding lower and upper frames 13 and 14 are, for example, made of polystyrene containing 4% by weight of carbon black in the form of dispersion, and are closely in contact with each other. The upper frame 14 has an opening in its upper surface, the opening being communicated with the chemical receptor 12 provided on the FET 11. A light-shielding cover 16 made of opaque-coated metal or plastic material is provided to cover the opening. The light-shielding cover 16 has a sample liquid supply port 15 in its upper surface and is partitioned into two, upper and lower parts by a partition plate 16a. The partition plate 16a has opening 17 formed at a position away from the liquid supply port 15 and provided to permit the sample liquid to pass through. The sample liquid can pass through the opening 17, but light incident from the liquid supply port 15 can not pass through the opening 17 except slight scattered light. Further, the partition plate 16a has an air-vent pipe 18 communicated with the outside. The air-vent pipe 18 has a cover 18a. The cover 18a prevents light from passing through the air-vent pipe 18 so as not to reach the FET. In FIG. 2A, the reference numerals 11d and 11e designate terminals for electrical connection to the source and drain regions of the FET 11.

Figure 3A:
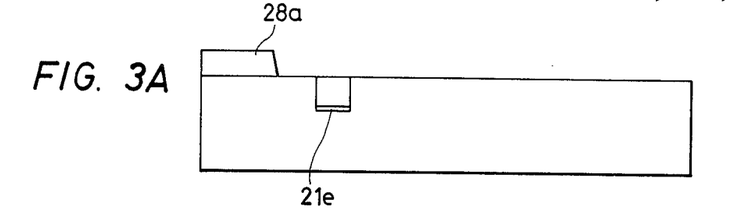
FIGS. 3A and 7A are elevational views of the chemical sensor according to the present invention.
Figure 3B:
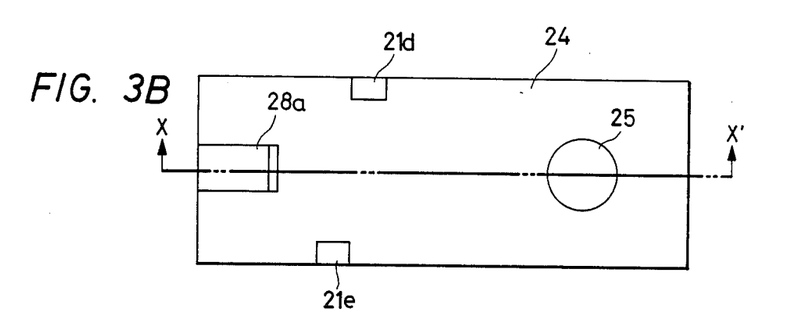
Figure 3C:
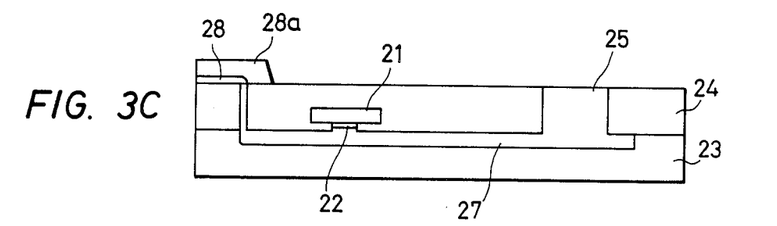

FIG. 3A is an elevational view showing a third embodiment of the FET sensor package, FIG. 3B is a plan view thereof, and FIG. 3C is a sectional view taken along the line X—X' of FIG. 3B. In FIGS. 3A to 3C, the package for housing the FET 21 is composed of a lower frame 23 and an upper frame 24, both made of light-shielding material. The FET 21 is embedded in the upper frame 24, and the chemical receptor 22 of the sensor is communicated with a liquid passage 27 provided on the upper surface of the lower frame 23. The sample liquid supplied from the liquid supply port 25 passes through the liquid passage 27 so that the sample liquid can be brought into contact with the chemical receptor 22. An air vent 28 is provided at an end of the liquid passage 27. A cover 28a of the air vent 28 prevents light from passing through the air-vent pipe 28 into the inside. In FIG. 3B, the reference numerals 21d and 21e designate terminals for electrical connection to the source and drain regions of the FET 21 respevtively.

Figure 3D:
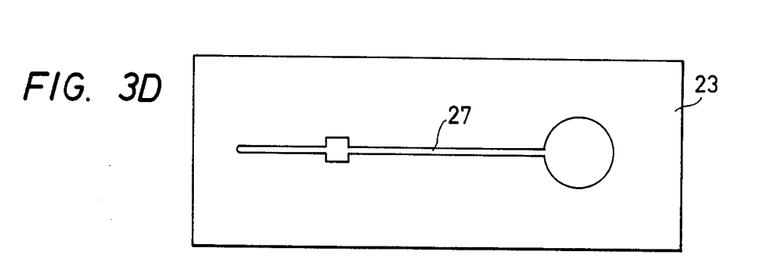
FIGS. 3D, 4B, 5C, 6C and 6D are plan views showing part of the chemical sensor according to the present invention.

FIG. 3D is a plan view housing, showing the upper surface of the lower frame 23 of the sensor. The contact surfaces of the lower and upper frames being at least in contact with the sample liquid must be chemically inactive to the sample liquid. If the sample liquid has its origin in a living body, the surfaces must be biochemically inactive. If the sample liquid is blood, it is preferable that the surfaces are made of material free from hemolysis. At least one part of the liquid passage 27 may be provided at the lower surface of the upper frame 24.

Figure 4A:
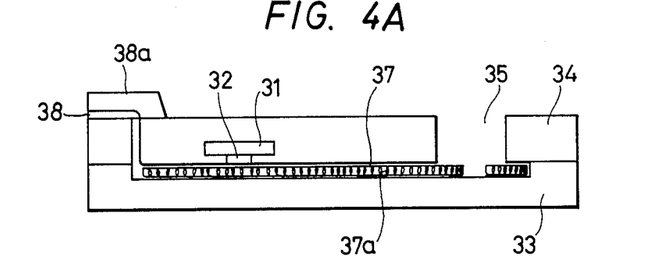
Figure 4B:
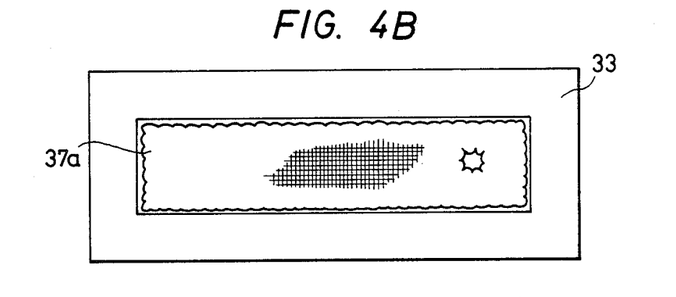

FIG. 4A is a sectional view of a fourth embodiment of the sensor package having its outside appearance as shown in FIGS. 3A and 3B, the view of FIG. 4A being taken along the line X—X' of FIG. 3B. The embodiment of FIG. 4A is substantially the same as that of FIG. 3C, except that cloth 37a *is provided in the liquid passage 37. The cloth 37a* must be chemically inactive to a sample liquid. If the sample liquid has its origin in a living body, the cloth 37a must be biochemically inactive. If the sample liquid is blood, it is preferable that the cloth 37a is made of material free from hemolysis. The sample liquid is fed to the cloth 37a from the supply port 35, permeates through the cloth 37a and reaches the chemical receptor 32 of the sensor. An air vent 38 is provided at an end of the liquid passage 37. FIG. 4B is a part view showing the upper surface of the lower frame 33 in the condition that the upper frame 34 of the package is removed.

Figure 5A:
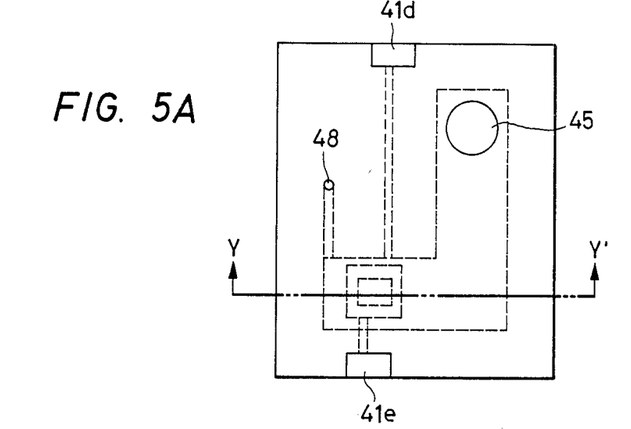
Figure 5B:
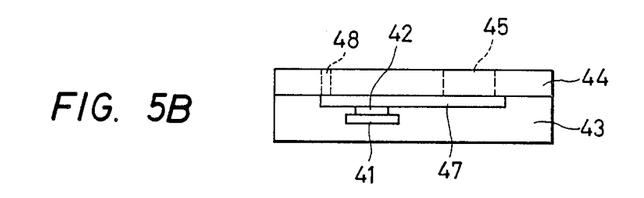
Figure 5C:
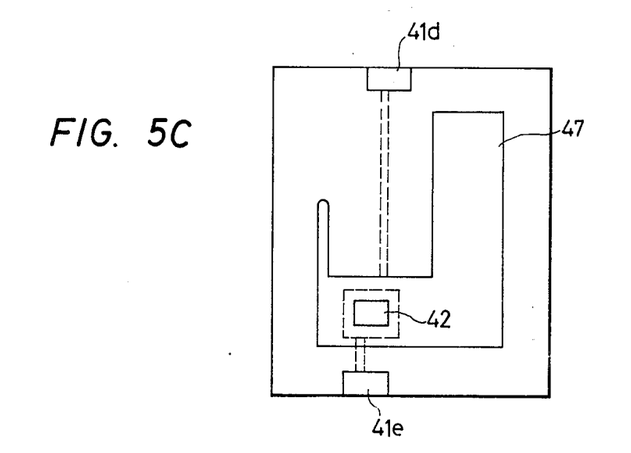

FIG. 5A is a plan view of a fifth embodiment of the sensor package, and FIG. 5B is a sectional view taken along the line Y—Y' of FIG. 5A. The liquid passage 47 is disposed between the light-shielding upper and lower frames 44 and 43. The FET is embedded in the lower frame 3, and the chemical receptor 42 faces the liquid passage 47. In FIG. 5A, the reference numerals 41d and 41e designate terminals for electrical connection to the source and drain regions of the FET 41 respectively. FIG. 5C is a part view showing the upper surface of the lower frame 3 in the condition that the upper frame 44 of the package is removed. The liquid passage 47 is bent to be L-shaped in plan as shown in FIG. 5C, so that light from the supply port 45 can hardly reach the FET 41. The air within the liquid passage 47 can be drawn out of an exhaust port 48. In order to transmit the sample liquid, cloth may be provided in the liquid passage 47. If the sample liquid is whole blood, long-staple cellulose nonwoven fabric or the like is suitable because hemolysis hardly occurs.

Figure 6A:
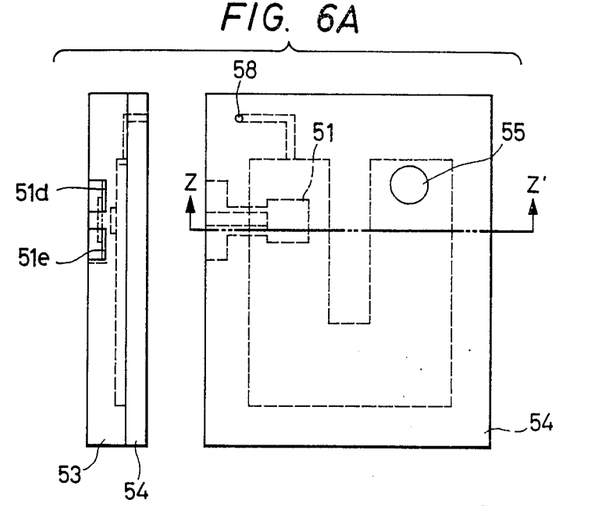
Figure 6B:
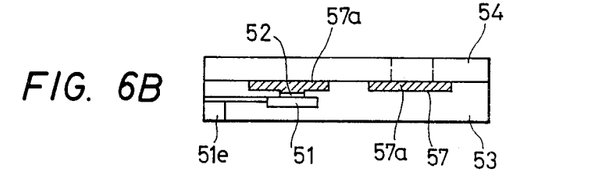
Figure 6C:
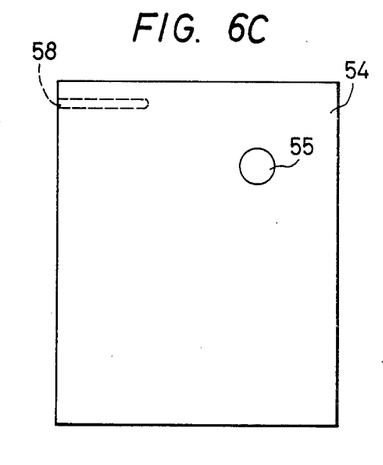
Figure 6D:
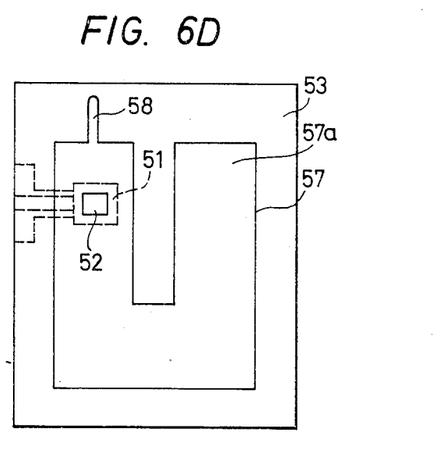

FIG. 6A is a plan and elevational view of a sixth embodiment of the sensor package, and FIG. 6B is a sectional view taken along the line Z—Z' of FIG. 6A. The liquid passage 57 is disposed between the upper and lower light-shielding frames 54 and 53. The FET is embedded in the lower frame 53, and the chemical receptor 52 faces the liquid passage 57. In FIG. 6A, the reference numerals 51d and 51e designate terminals for electrical connection to the source and drain regions of the FET 51. FIG. 6C is a part view showing the upper surface of the upper frame 54 of the package, and FIG. 6D is a part view showing the upper surface of the lower frame 53 in the condition that the upper frame 54 of the package is removed. The liquid passage 57 is curved to be U-shaped in plan view as shown in FIG. 6D, so that light from the supply port 55 can hardly reach the FET 51. The sample liquid passes through the passage 57 from the supply port 55 and then reaches the chemical receptor 52 of the sensor. The air within the liquid passage 57 can be drawn out of an exhaust port 58. In order to transmit the sample liquid, cloth 57a (such as for example long-staple cotton nonwoven fabric) may be provided in the liquid passage 57.

Figure 7A:
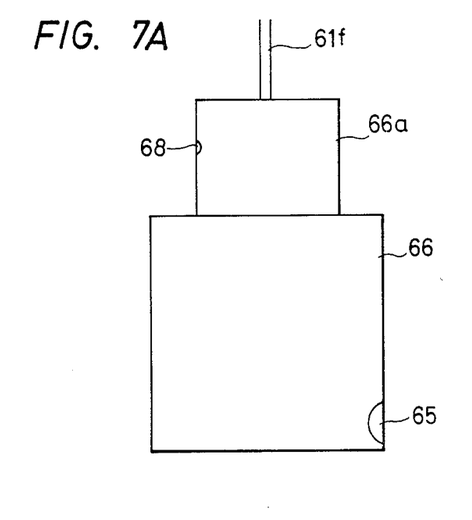
Figure 7B:
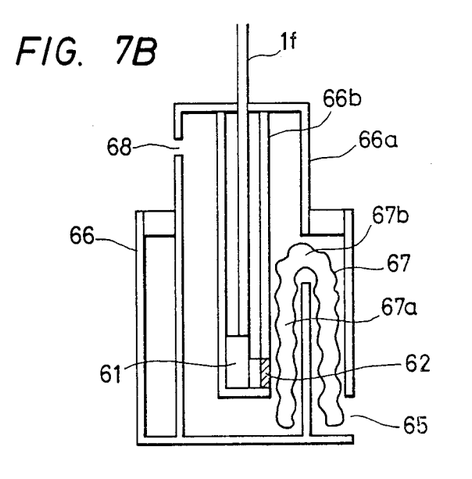

FIG. 7A is an elevational view of a seventh embodiment of the sensor package, and FIG. 7B is a sectional view taken perpendicularly thereto. The sensor shown in the drawing is suitable for use while being soaked in the sample liquid. The sensor is fixed to an end of a light-shielding pipe 66a which is fixed to the center of a double cylinder 66, 66a made of light-absorptive material. The sensor provided at the end of the center pipe 66a is surrounded by the light-shielding outer and inner cylinder 66 and 66a. The liquid passage 67 is formed between the light-shielding outer and inner cylinders 66 and 66a and between the inner cylinder 66a and the center pipe 66b. A liquid-transport member 67a (such as for example long-staple cellulose nonwoven fabric) is provided within the liquid passage 67. The FET 61 is sealed up in the pipe 66a provided at the center of the inner cylinder 66a, and the chemical receptor 62 faces the liquid passage 67 through the opening. In the drawing, the reference numeral 61f designates lead wire for electrical connection to the source and drain regions of the FET 61. The outer cylinder 66 has a liquid supply port 65 at its lower end, and the inner cylinder 66a has an opening 67b disposed at a position away from the liquid supply port 65 and provided to permit the sample liquid to pass through. The sample liquid supplied from the sample liquid supply port 65 is allowed to pass through the solution-transport member 67a in the opening 67b, so that the sample liquid can reach the chemical receptor 62 of the sensor. Contrarily, light incident from the solution supply port 65 can hardly pass through the opening 67b into the sensor portion. The outer and inner cylinders 66 and 66a must be chemically inactive to the sample liquid. Further, the inner cylinder 66a has a small-sized air-vent port 68 disposed at an upper end thereof and communicated with the outside. Although FIG. 7A shows the case where each of the outer cylinder 66, inner cylinder 66a and center pipe 66a is round in section, it is to be understood that the invention is not limited to the specific embodiment and that each of them may be suitably shaped. For example, each of them may be shaped in a polygon, such as a triangle, a rectangle, a hexagon, an oxtagon or the like, or may be shaped like an ellipse or oval in section.

The use of the sensor in accordance with the present invention produces the effect that the measurement can be carried out without groping equipment, such as measuring machines and experimental arrangements brought into a darkroom; analyzers brought into a darkbox; and the like. EXA

MPLE OF MEASUREMENT

Urea in a sample liquid, buffered at a pH of 7.3 was detected by an urea sensor having urease immobilized by albumin and glutaraldehyde at the gate of an ISFET. The measurement was carried out with the urea sensor without casing placed in a room illuminated with two 40-watts straight tube fluorescent lamps from the ceiling of the room. Electric potential varied in a range of about 2 mV in case the sample contained no urea, and in a range of 4 mV in case the sample contined urea.

The measurement carried out in the same manner as described above using an urea sensor housed in the package of FIGS. 7A and 7B resulted in electric potentials varying in a range of 0.5 mV or less. Furthermore, the abosolute values of the electric potential were about 10 mV higher compared to the above measurement carried out with the urea sensor exposed to the light.

What is claimed is:

1. In a chemical sensor device for analyzing a specific substance in a liquid, comprising a chemical receptor for chemically reacting said specific substance in a sample liquid and a field effect transistor connected to said chemical receptor for converting the chemical reaction into a measurable electrical signal, the improvement which comprises;

said field effect transistor connected to said chemical receptor being installed in a housing having light-shielding properties, said housing having an opening portion which receives and introduces to said chemical receptor the sample liquid and a light-shielding means which substantially prevents external light from reaching said field effect transistor but permits the sample liquid to reach said chemical receptor; said light-shielding means comprising a liquid-permeable and light-absorptive porous member for covering said opening portion; and, channel means for conveying the sample to said chemical receptor.

2. A chemical sensor device as claimed in claim 1, wherein said porous member comprises any one of cotton cloth, cotton knitting and long-staple cellulose nonwoven fabric, and any one of a light-absorptive dye and pigment incorporated therein.

3. A chemical sensor device as claimed in claim 1, wherein said chemical means is U-shaped in plane.

4. In a chemical sensor device for analyzing a specific substance in a liquid, comprising a chemical receptor for chemically reacting said specific substance in a sample liquid and a field effect transistor connected to said chemical receptor for converting the chemical reaction into a measurable electrical signal, the improvement which comprises;

said field effect transistor connected to said chemical receptor being installed in a housing having light-shielding properties, said housing having an opening portion which receives and introduces to said chemical receptor the sample liquid and a light-shielding means which substantially prevents external light from reaching said field effect transistor but permits the sample liquid to reach said chemical receptor; said light-shielding means comprising a light-shielding chamber having a sample liquid supply port and a partition plate for partitioning said light-shielding chamber into upper and lower parts, said partition plate having an opening formed at a position distant from said liquid supply port to permit sample liquid to pass therethrough and shielding external light from said sample liquid supply port and including an air-vent pipe leading to the outside of said light-shielding means.

5. A chemical sensor device as claimed in claim 4, wherein said air-vent pipe has a cover at one end thereof for preventing light from passing therethrough.

6. In a chemical sensor device for analyzing a specific substance in a liquid, comprising a chemical receptor for chemically reacting said specific substance in a sample liquid and a field effect transistor connected to said chemical receptor for converting the chemical reaction into a measureable electrical signal, the improvement which comprises;

said field effect transistor connected to said chemical receptor being installed in a housing comprising a liquid-permeable and light-absorptive porous member for covering said opening portion, having light-shielding properties, said housing having an opening portion which receives and introduces to said chemical receptor the sample liquid and a light-shielding means, including a cloth inert to said sample liquid, which substantially prevents external light from reaching said field effect transistor but permits the sample liquid to reach said chemical receptor; and wherein said housing has an L-shaped liquid passage for transporting said sample liquid from said opening portion to said chemical receptor extending longitudinally to said housing and connected with said opening portion at one end thereof and wherein an air-vent is provided in said housing and said liquid passage is connected with said opening portion at one end thereof and with said air-vent at the other end.

7. A chemical sensor device as claimed in claim 6, wherein said chemical receptor connected with field effect transistor is located at a position between both ends of said liquid passage.

8. A chemical sensor device as claimed in claim 6, wherein said liquid passage is bent to be L-shaped in plane.

9. A chemical sensor device as claimed in claim 6, wherein said cloth chemically is inert to said sample liquid an is provided with said liquid passage.

10. A chemical sensor device as claimed in claim 6, wherein said housing comprises a dual cylinder closed at both ends comprising an inner cylinder and an outer cylinder surrounding at least partially said inner cylinder, said inner cylinder having a member holding said field effect transistor enclosed therein and said chemical receptor communicated with the inside of said inner cylinder.

11. A chemical sensor device as claimed in claim 6, wherein a first opening for receiving said sample liquid into said outer cylinder is formed at a lower end of said outer cylinder, a second opening for leading said sample liquid further to the inside of said inner cylinder is formed through said inner cylinder at a position remote from said first opening; and air-vent open to the outside of the housing is formed at an upper end of said inner cylinder.

12. A chemical sensor device as claimed in claim 6, wherein said second opening is formed at the upper end of said inner cylinder.

13. The chemical sensor device of claim 6, wherein the cloth is made from a material selected from the group consisting of cotton knitting and non-woven fabric.

14. The chemical sensor of claim 6, wherein said cloth includes a light-absorptive dye of pigment.

* * * * *